US005182358A

United States Patent [19]

Hay et al.

[11] Patent Number: 5,182,358

[45] Date of Patent: Jan. 26, 1993

[54] POLYMERS AND COPOLYMERS OF HIGH GLASS TRANSITION TEMPERATURE FROM HINDERED PHENOLS

[76] Inventors: Allan S. Hay, 5015 Glencairn Ave., Montreal, Quebec, Canada, H3W 2B3; Whan Gi Kim, 3575 University Avenue, Montreal, Quebec, Canada, H3A 2B1

[21] Appl. No.: 683,860

[22] Filed: Apr. 11, 1991

[51] Int. Cl.[5] .............................................. C07C 39/12

[52] U.S. Cl. .................................... 528/191; 252/404; 528/98; 528/125; 528/126; 528/128; 528/219; 528/191; 568/730

[58] Field of Search ............... 528/125, 126, 128, 219, 528/98, 171, 191; 525/437, 450, 471, 397, 394; 524/425; 521/134

[56] References Cited

U.S. PATENT DOCUMENTS 3,720,721 3/1973 Becker et al. ........................ 528/191

*Primary Examiner*—John Kight, III
*Assistant Examiner*—Shelley Wright
*Attorney, Agent, or Firm*—Swabey Ogilvy Renault

[57] ABSTRACT

Polymers and copolymers having high glass transition temperature and which are soluble in organic solvents are produced from highly hindered biphenols, in particular polyetherketones, polyethersulfones, polyesters and polyetherimides, as well as copolymers based on these polymers may be produced for a variety of applications.

10 Claims, No Drawings

POLYMERS AND COPOLYMERS OF HIGH GLASS TRANSITION TEMPERATURE FROM HINDERED PHENOLS

BACKGROUND OF THE INVENTION i) Field of the Invention

This invention relates to polymers and copolymers of high glass transition temperature, and their synthesis from hindered phenols.

ii) Description of Prior Art

Polyetherketones are crystalline polymers which have a relatively low glass transition temperature (Tg) and a melting point (Tm) above 300° C. The commercial polymer, polyether etherketone has a Tg of 144° C. and a Tm of 335° C. P. M. Hergenrother et al, Polymer Preprints 26, 74 (1985) described the preparation of polyarylene ethers by the reaction of bis-1,3- and 1,4-(4-chlorobenzoyl) benzene with bisphenol-A, the resulting polymers have Tg's of 153° C. and 166° C., respectively.

Polyethersulfones are generally amorphous materials with Tg's higher than the polyetherketones. Commercial polyethersulfones have a Tg of about 210° C.

Polyesters also have many industrial applications; and polyetherimides such as those shown in U.S. Pat. No. 3,917,643 have a number of applications particularly as coatings.

It would be advantageous to provide polymer materials, including polymers and copolymers, of high glass transition temperature, thereby permitting use of the polymers in high temperature applications.

It would also be advantageous to provide such polymer materials which are soluble in readily available organic solvents, whereby production of coatings, films and parts from the polymer materials might be simplified.

SUMMARY OF THE INVENTION

It is an object of this invention to provide polymers and copolymers which have high glass transition temperatures and which are amorphous.

It is a further object of this invention to provide polymers and copolymers with high glass transition temperatures, and which are soluble in an organic solvent at room temperature.

It is a further object of this invention to provide such polymers and copolymers having units derived from highly hindered biphenols.

It is yet another object of this invention to provide a process for the synthesis of such polymers and copolymers from hindered biphenols.

In accordance with the invention polymer substances of the invention may be represented by the formula (I):

$$-[(A)_x(B)_y]- \qquad (I)$$

in which:

A indicates monomer units derived from highly hindered biphenols;

B indicates comonomer units of formula:

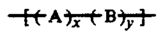

in which:

$C_p$ is derived from a comonomer and Z is as defined hereinafter;

x is an integer of at least 1;

y is 0 or an integer of at least 1;

$x+y=n$; and n is an integer of 2 to 200.

Thus when y is 0, the polymer substance is a homopolymer containing only the units of the hindered biphenol, and when y is an integer of 1 or more, the polymer substance is a copolymer.

It will be recognizes that x and y indicate the total number of the units A and B, respectively, and not the sequence of the units.

The hindered biphenol units A are in particular of formula (II):

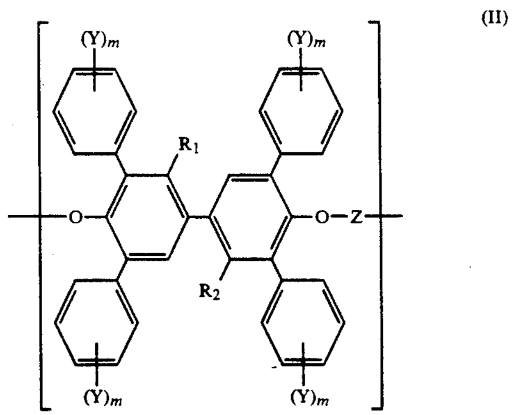

wherein:

$R_1$ and $R_2$ are the same and are selected from methyl, phenyl, naphthyl, p-fluorophenyl, p-chlorophenyl and p-bromophenyl, or one of $R_1$ and $R_2$ is hydrogen and the other is chlorine;

Y is fluorine;

m is 0, 1, 2, 3, 4 or 5; and

Z is a divalent linkage of formula:

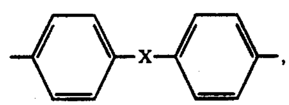

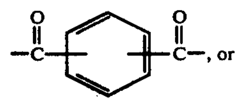

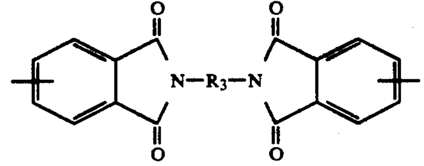

in which X is —CO— or —$SO_2$—, and $R_3$ is an aromatic hydrocarbon radical or aromatic hydrocarbon ether radical having from 6 to 20 carbon atoms, and halogenated derivatives thereof.

In another aspect of the invention there is provided a process for preparing a polymer or copolymer of formula (I) which comprises reacting a hindered phenol with a source of the divalent linkage Z.

The hindered phenols are of formula (III):

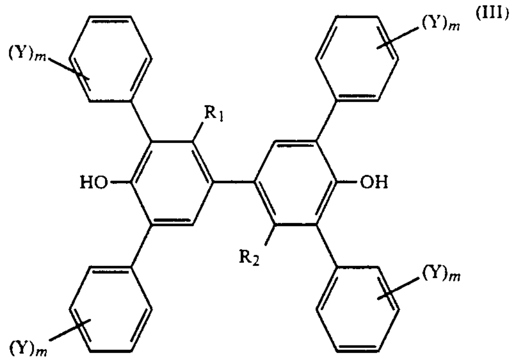

in which $R_1$, $R_2$, Y and m are as defined above.

The source of the divalent linkage Z is, in particularly, a dihalobenzophenone or dihalodiphenylsulfone, in which the halo is fluorine or chlorine, when a polyetherketone or polyethersulfone is desired; and a 1,3- or 1,4-benzenedicarbonyl dichloride, for example, isophthalaloyl dichloride when an ester is desired.

In the case of the polyetherimides, the hydroxyl groups of the hindered phenol of formula (III) are first converted to the corresponding 3,4-dicarboxyphenoxy anhydride groups and the resulting dianhydride is reacted with a compound of formula (XI):

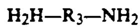

$$H_2H—R_3—NH_2 \quad (XI)$$

in which $R_3$ is an aromatic hydrocarbon radical or aromatic hydrocarbon ether radical having from 6 to 20 carbon atoms and halogenated derivatives thereof.

The aromatic hydrocarbon radical may, for example, be phenylene or a bis(phenylene) ether radical.

It will be understood that the aromatic divalent radicals $R_3$ may include alkyl moieties as part of the 6 to 20 carbon atoms, and ay include two or more aromatic nuclei, which nuclei may be fused as in naphthylene or non-fused as in biphenylene.

It will be understood that if copolymers are required then the source of the copolymer units is included in the reaction mixture in an appropriate amount relative to the hindered phenol or its derivative, having regard to the characteristics desired in the copolymer.

Clearly the copolymer units B must be derived from a source which will react with the source of the divalent linkage Z, and in this way some of the units A in the polymer chain are replaced by the copolymer units B.

DESCRIPTION OF PREFERRED EMBODIMENTS i) Polyetherketones and Polyethersulfones

The polymers of the invention are polyetherketones when Z is a divalent radical:

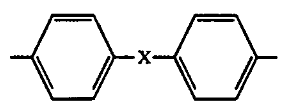

and X is a radical —CO—, and are polyethersulfones when X is a radical $—SO_2$.

Polyetherketones and polyethersulfones are preferred in which $R_1$ and $R_2$ are both methyl or both phenyl, and m is 0, and n is an integer of 50 to 150.

The polyether etherketones and sulfones of the invention are amorphous and very soluble in methylene chloride at room temperature. As such the polymers can be cast into tough flexible films for high temperature applications from a solution in methylene chloride solvent.

Table 1 below shows characteristics of particular polyetherketones and sulfones of the invention in which m is 0.

TABLE 1

| $R_1$ | $R_2$ | X | Tg[a] | ηinh[b] | Mw × 10[c]3 |
|---|---|---|---|---|---|
| Ph | Ph | $SO_2$ | 265 | 0.18 | 36.4 |
| Ph | Ph | CO | 265 | 0.46 | 162.3 |
| $CH_3$ | $CH_3$ | $SO_2$ | 285 | 0.83 | 213.9 |
| $CH_3$ | $CH_3$ | CO | 285 | 0.59 | 141.4 |
| H | Cl | $SO_2$ | 280 | 0.19 | 44.5 |
| H | Cl | CO | 230 | 0.09 | 6.8 |

(a) DSC analyses were done on a Mettler FP 80 instrument at a rate of 20° C./min.

(b) Inherent viscosities were measures in chloroform at 25° C.

(c) Molecular weights were determined by gel permeation chromatography using polystyrene standards with chloroform as solvent on a Waters 510 HPLC with a UV detector with four μstyragel columns (500, $10^4$, $10^5$ & 100 Å) in series.

The polyetherketones are prepared by reacting a hindered biphenol of formula (III) with difluorobenzophenone or dichlorobenzophenone; whereas the polyethersulfones are prepared by reacting the hindered biphenol of formula (III) with difluorodiphenylsulfone or dichlorodiphenylsulfone.

The reaction is most suitably carried out in the presence of a base, for example potassium carbonate, in a polar, aprotic solvent under refluxing conditions.

Suitable polar aprotic solvents include dimethylsulfoxide, dimethylacetamide and N-methylpyrrolidone.

ii) Polyesters

The polymers of the invention are polyesters when Z is a divalent radical:

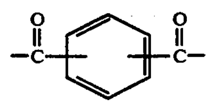

Preferably the carbonyl groups are in the 1,3- or 1,4-position.

The polyesters are produced by reacting the hindered biphenols with 1,3- or 1,4-benzenedicarbonyl chlorides, suitably under reflex conditions in the presence of zinc as a catalyst.

iii) Polyetherimides

The polymers of the invention are polyetherimides when Z is a divalent radical:

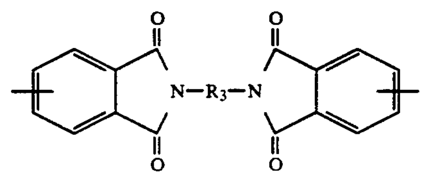

in which $R_3$ is as defined hereinabove.

The polyetherimides are produced from derivatives of the hindered biphenols of formula (III). In particular the hindered biphenols of formula (III) are converted at their hydroxyl radicals to the corresponding 4,4-bis(3,4-dicarboxyphenoxy)dianhydrides, which are reacted with aromatic diamines to produce the polyetherimides.

The polymerization is suitably carried out in a solvent, for example N-methyl-2-pyrrolidinone, at room temperature, under an inert atmosphere, for example nitrogen, to produce the polyamic acid followed by heating to effect the imidization reaction and produce the final polyetherimide product.

iv) Copolymers

The copolymers are produced by including in the reactants a suitable comonomer which will react with the linking compound.

Suitably the comonomer is an aromatic bisphenol, for example hydroguinone, 4,4'-dihydroxybiphenol or bisphenol A.

In particular the comonomer may be a different hindered biphenol of formula (III), so that the A and B units are both of formula (II). The comonomer B may also comprise a biphenol which is less hindered than the biphenol of formula (III), for example 3,3',5,5'-tetraphenol-[1,1'-biphenyl]-4,4'-diol.

Furthermore the copolymer may include some units B which are units of formula (II) different than the units A, and some units B which are derived from other bisphenols, especially less hindered biphenols.

The copolymer may comprise the A and B units in a random or ordered arrangement along the copolymer chain; thus the invention contemplates such diverse segments as:

| |
|---|
| —ABABAB— |
| —AABAABAAB— |
| —AAAAABAABA— |
| —AABBABAAABA— |
| —AAAA—BBBB— |

The proportions of A and B units in the copolymer are dependent on the relative amounts of the hindered biphenol and comonomer in the polymerization medium; in addition the sequence can be controlled, at least in part, by delaying addition of comonomer to the polymerization medium.

v) Hindered Biphenols

The hindered biphenols of formula (III) in which $R_1$ and $R_2$ are the same can be produced by the oxidative coupling of a phenol of formula (IV):

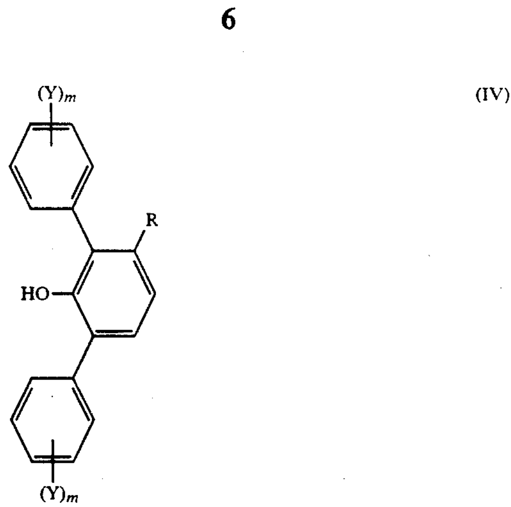

in which R is methyl, phenyl, naphthyl, p-fluorophenyl, p-chlorophenyl or p-bromophenyl, and Y and m are as defined previously.

The oxidative coupling is carried out with oxygen in the presence of cuprous ions according to the procedure described by A. S. Hay in J. Org. Chem., 36, 218 (1971).

The starting phenols (IV) are prepared by known procedures. For example, 2,3,6-triphenylphenol (2a) and 2,6-diphenyl-3-methylphenol (2b) are prepared by reaction of dibenzylketone and cinnamaldehyde or but-2-enal in the presence of diethylamine, followed by dehydrogenation of the intermediate cyclohexanone on a Pd/C catalyst in accordance with Scheme 1.

Scheme 1

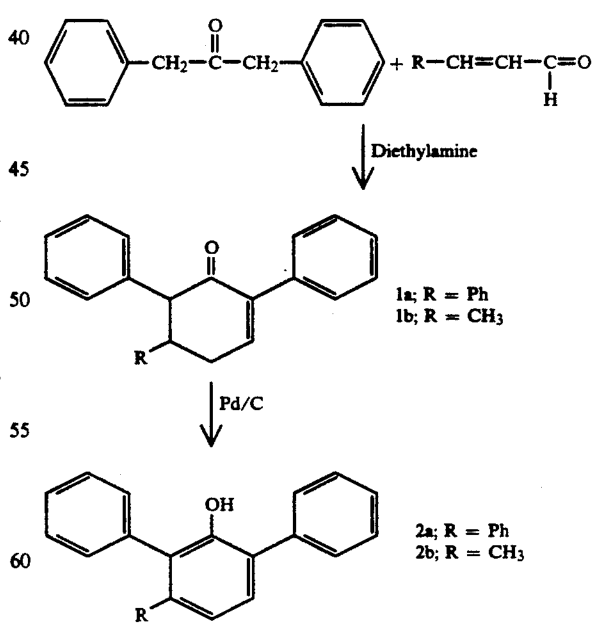

The chlorotetraphenylbiphenol is prepared by the addition of hydrogen chloride to tetraphenyldiphenoquinone in accordance with U.S. Pat. No. 3,720,721, as illustrated in Scheme 2:

Scheme 2

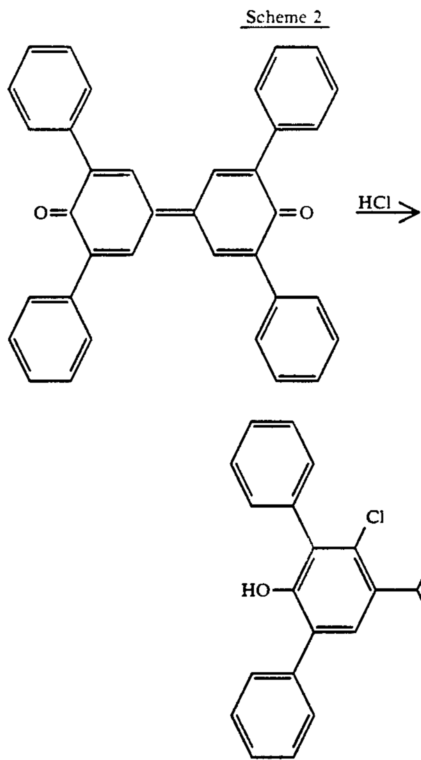

It was surprising that the biphenols of formula (III) would react to produce polymers since they are highly hindered and it would have been expected that they would be too sterically hindered to react.

It appears that the biphenols (III) have a rigid structure in which the biphenyl moieties are not coplanar.

Attempts to synthesize polymers from the less hindered 3,3′,5,5′-tetraphenylbiphenol were not successful. The polyetherketone was found to be highly crystalline and only low molecular weight polymer could be produced because the polymer was precipitated during synthesis. The polyethersulfone was produced but has a lower glass transition temperature than the polymers (III), and was also less soluble.

The lack of success with the less hindered phenols is a further indication of the surprising result achieved with the highly hindered biphenols in producing amorphous polymers of high Tg and high solubility at room temperature in methylene chloride.

Synthesis of Polysulphones; Homopolymers and Copolymers

The polymers were synthesized by nucleophilic displacement of 4,4′-difluorodiphenylsulphone with one or more bisphenols.

EXAMPLES

Example 1. Synthesis of 2,2′-dimethyl-3,3′,5,5′-tetraphenyl-[1,1′-biphenyl]-4,4′-diol To a 250 mL three necked round bottom flask, equipped with a condenser and magnetic stirrer was added 100 g (0.48 mol) of diphenylacetone and 33.3 g (0.48 mol) of acrolein, 50 mL of diethylamine and 10 mL of triethylamine. After reacting for 3 hours at room temperature methanol was added to the reaction mixture and the product crystallized to yield 101 g (85%) of 3-methyl-2,6-diphenyl-2-cyclohexanone, m.p.: 99°-101° C. Dehydrogenation of 80 g (0.32 mol) of this product in the presence of 4 g of 5% palladium on carbon catalyst was carried out for 20 min at 260° C. The reaction mixture was cooled and dissolved in hot ethanol and filtered to yield 65.1 g (83%) of 2,6-diphenyl-3-methylphenol. 50 g of 2,6-diphenyl-3-methylphenol was treated with 3.8 g of CuCl and 400 mL of butyronitrile. The reaction was heated to 100° C. while passing oxygen through for 4 hours. A while solid precipitated during the reaction.

The heterogeneous solution was cooled down and filtered. It was recrystallized from ethanol and chloroform to yield (44.6 g, 85%). m.p.: 279°-280° C. 1H NMR (200 MHZ, $CDCl_3$) δ1.87 (s, 6H, methyl), δ4.96 (s, 2H, OH) δ723-7.63 (m, 22H, ArH).

Example 2. Polymerization of 2,2′-dimethyl-3,3′,5,5′-tetraphenyl-[1,1′-biphenyl]-4,4′-diol with 4,4′-difluorodiphenylsulphone

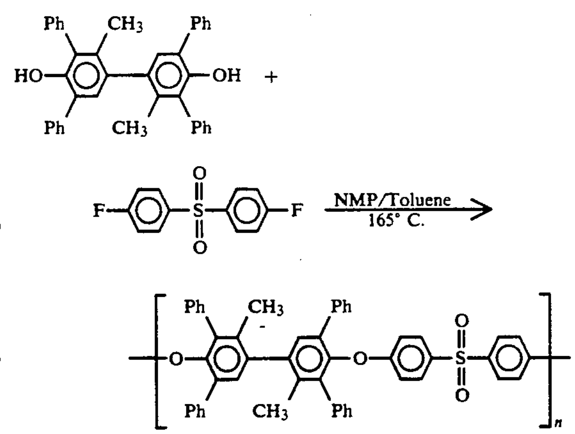

To a 50 mL three necked round bottom flask, fitted with a condenser, Dean-Stark trap and nitrogen inlet, there was added 0.64 g (2.5 mol) of 4,4′-difluorodiphenylsulphone and 1.30 g (2.5 mol) of 2,2′-dimethyl-3,3′,5,5′-tetraphenyl-[1,1′-biphenyl]-4,4′-diol (0.0025 moles) in N-methylpyrrolidinone (5 mL). Toluene (3 mL) was added along with potassium carbonate (30% excess). The reaction mixture was stirred vigorously and heated to reflux at 155° C. and maintained for 4 hours until no more water droplets separated. Toluene was then removed continuously from the trap until the temperature rose to about 165° C. and kept there for 70 hours. At this time the solution was very viscous. The reaction was checked by HPLC to demonstrate the absence of starting materials. The solution first became yellow (65° C.), then green, and finally dark green. The reaction mixture was cooled to about 110° C. and NMP 3 mL) was added to dilute the highly viscous solution. It was then extracted to remove the excess salts with 4% HCl solution and the solution was precipitated in methanol to give a fibrous polymer (83% yield). The polymer was characterized by NMR, which showed a methyl peak at 1.9 ppm and the ratio of the number of protons (phenyl to methyl) is 5:1 as expected. The two protons of the biphenol gave a doublet at 6.3 ppm. The polymer was soluble in NMP, chloroform, methylene chloride, and insoluble in acetone and methanol. The polymer has a glass transition temperature (Tg) of 284° C. determined in a DSC at 10° C./min. It could be cast into a flexible transparent film. The polymer had an inherent viscosity of 0.83 (0.5% solution in $CHCl_3$@25° C.) and a weight average molecular weight of 213,900. The polymer shows a 5% weight loss at 475° C. by thermogravimetric analysis.

Example 3. Synthesis of 2,2',3,3',5,5'-hexaphenyl-[1,1'-biphenyl]-4,4'-diol 2,3,6-Triphenylphenol was prepared according to A. S. Hay and R. F. Clark (Macromolecules, 3, 533, 1970). 11.36 g (54 mmoles) of dibenzylketone, 7.14 g (54 mmoles) of cinnamaldehyde and 5 mL of diethylamine were mixed and the solution became yellow and after 20 min. a yellow solid deposited. The solid was added to ethanol (80 mL), cooled and filtered to yield 2,3,6-triphenylcyclohexenone (91%). The product (8.0 g) was mixed with 1 g of 5% Pd on carbon and heated at 270° C. for 30 min and then cooled. The mixture was dissolved in hot ethylacetate and the hot solution was filtered and cooled to yield 2,3,6-triphenylphenol (69%). The oxidation of triphenylphenol (5 g) was carried out in butyronitrile (50 mL) with a CuCl catalyst (0.4 g) by passing oxygen through the stirred solution at 100° C. for 8 hours. The reaction mixture was cooled and filtered to yield (82%) of the crude biphenol. Reduction with a few drops of hydrazine in hot acetic acid reduced any of the diphenoquinone in the product to give 2,2',3,3',5,5'-hexaphenyl-[1,1'-biphenyl]-4,4'-diol which was further purified by crystallization.

Example 4. Polymerization of 4,4'-difluorodiphenylsulphone with 2,2',3,3',5,5'-hexaphenyl-[1,1'-biphenyl]-4,4'-diol

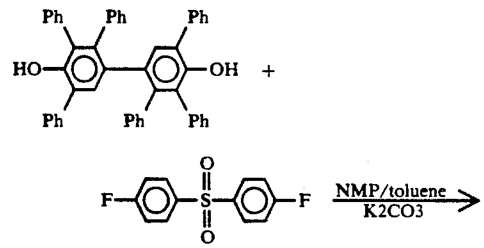

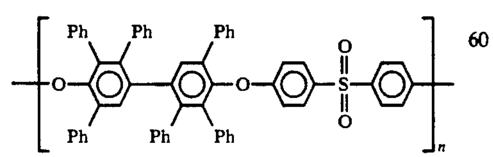

The polymerization was carried out and the polymer isolated as described in Example 1. The 2,2',3,3',5,5'-hexaphenyl-[1,1'-biphenyl]-4,4'-diol dissolved with a yellow color in NMP at 85° C. and changed to dark yellow when potassium carbonate was added and then became dark brown after a further 24 hours. The reaction was stopped after a further 48 hours. The polymer could be cast into a film which was brittle. It has a Tg of 256° C. The polymer has an inherent viscosity of 0.18 and a weight average molecular weight of 36,400. The polymer showed a 5% weight loss at by 531° C. by thermogravimetric analysis.

Example 5. Polymerization of 3,3',5,5'-tetraphenyl-[1,1'-biphenyl]-4,4'-diol and 4,4'-difluorodiphenylsulphone

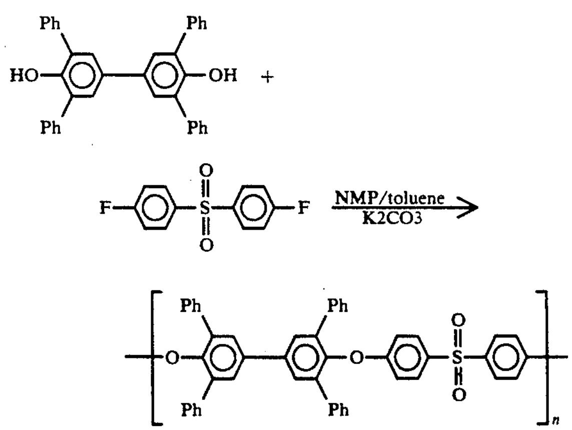

This reaction was carried out as in example 1 at 180° C. The polymer obtained in 78% yield was crystalline and could be cast into a translucent film. The polymer had an inherent viscosity of 0.33. The polymer showed a 5% weight loss at 525° C. by thermogravimetric analysis.

Example 6. Copolymerization of 2,2'-dimethyl-3,3',5,5'-tetraphenyl-[1,1'-biphenyl]-4,4'-diol (A) and 3,3',5,5'-tetraphenyl-[1,1'-biphenyl]-4,4'-diol (B) with 4,4'difluorodiphenylsulphone

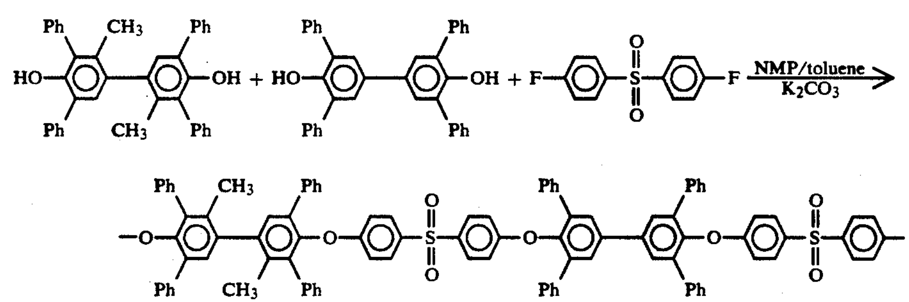

The copolymer was synthesized as in Example 1 using equimolar amounts of the two biphenols A and B. The polymer obtained could be cast into a flexible transparent film. The Tg is 275° C. and the polymer had an inherent viscosity of 0.42 and a weight average molecular weight of 84,900.

Example 7. Polymerization of 2,2',3,3',5,5'-hexaphenyl-[1,1'-biphenyl]-4,4'-diol (A) and 3,3',5,5'tetraphenyl-[1,1'-biphenyl]-4,4'-diol (B) with 4,4'-difluorodiphenylsulphone

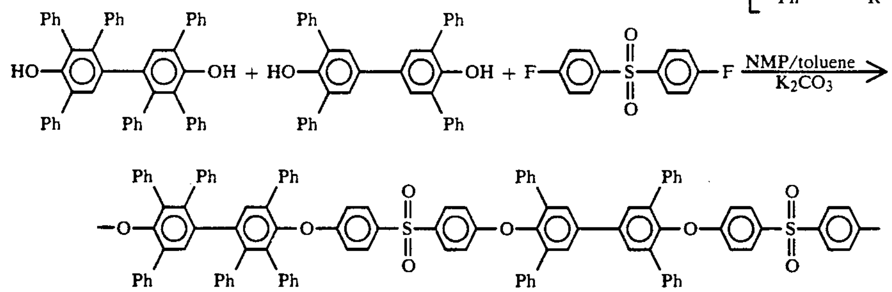

The copolymer was synthesized as in Example 1 using equimolar amounts of the two biphenols A and B. The polymer obtained could be cast into a transparent brittle film. The Tg is 265° C. and the polymer had an inherent viscosity of 0.13 and a weight average molecular weight of 11,300.

Example 8. Polymerization of 2-chloro-3,3',5,5'-tetraphenyl-[1,1'-biphenyl]-4,4'-diol and 4,4'-difluorodiphenylsulphone

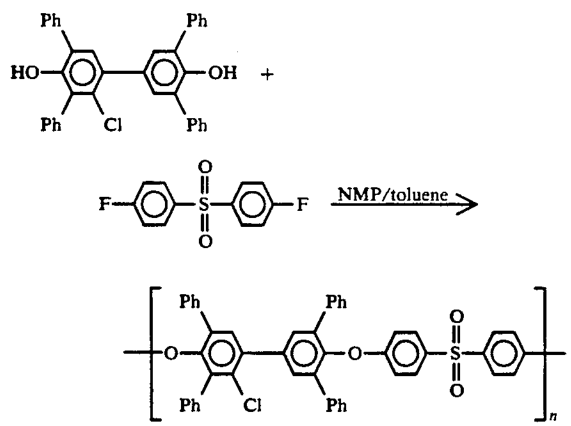

The polymerization was carried out as in Example 1 to give a polymer (90% yield) which could be cast into a transparent film. The Tg is 280° C. and the polymer had an inherent viscosity of 0.19 and a weight average molecular weight of 44,500.

Example 9. Polymerization of 2,2'-dimethyl-3,3',5,5'-tetraphenyl-[1,1'-biphenyl]-4,4'-diol and 4,4'-difluorobenzophenone

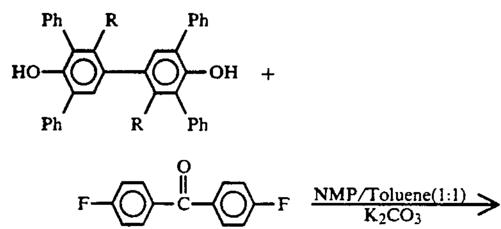

-continued

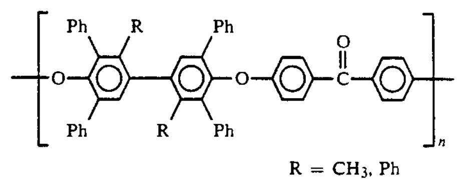

$R = CH_3$, Ph

This reaction was carried out according to the previous method except for the solvent system (1:1 ratio) and temperature conditions (180° C.). The polymer (83% yield) gave a very flexible film. The Tg is 282° C. and the polymer had an inherent viscosity of 0.59 and a weight average molecular weight of 141,400. The polymer showed a 5% weight loss at 452° C. by TGA.

Example 10. Polymerization of 2,2',3,3',5,5'-hexaphenyl-[1,1'-biphenyl]-4,4'-diol and 4,4'-difluorobenzophenone This reaction was carried out according to the previous method. The reaction mixture became very viscous after 72 hours. The polymer formed a very flexible transparent film. Tg is 256° C. and the polymer had an inherent viscosity of 0.46 (0.5% solution in $CHCl_3$@25° C.) and a weight average molecular weight of 162,300. The polymer showed a 5% weight loss by 559° C. by TGA.

Example 11. Polymerization of 3,3',5,5'-tetraphenyl-[1,1'-biphenyl]-4,4'-diol and 4,4'-difluorobenzophenone

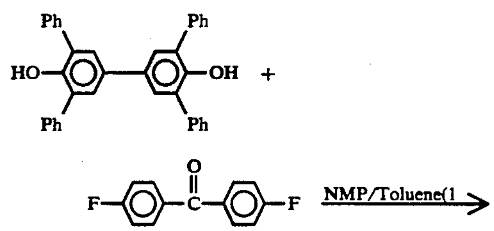

This reaction was carried out according to the previous method. In contrast to the previous polymerization reactions a solid separated from solution which was a low molecular weight crystalline polymer which didn't dissolve in NMP, chloroform or methylene chloride, Tg is 245° C.

Example 12. Copolymerization of 2,2'-dimethyl-3,3',5,5'-tetraphenyl-[1,1'-biphenyl]-4,4'-diol (A) and 3,3',5,5'-tetraphenyl-[1,1'-biphenyl]-4,4'-diol (B) with 4,4'-difluorobenzophenone.

The copolymerization was carried out with a molar ratio of 50 mol percent each of unit A and unit B. It was soluble and gave a flexible transparent film. Tg is 275° C. and the polymer had an inherent viscosity of 0.25 and a weight average molecular weight of 56,200.

Example 13. Copolymerization of 2,2',3,3',5,5'-hexaphenyl-]1,1'-biphenyl]-4,4'-diol (A) and 3,3',5,5'-tetraphenyl-[1,1'-biphenyl]-4,4'-diol (B) with 4,4'-difluorobenzophenone.

The copolymerization was carried out with a molar ratio of 50 mol percent each of unit A and unit B at 180° C. It was soluble and gave a brittle transparent film. Tg is 245° C. and the polymer had an inherent viscosity of 0.12 and a weight average molecular weight of 14,300.

Example 14. Synthesis of 2-chloro-3,3',5,5'-tetraphenyl-[1,1'-biphenyl]-4,4'-diol (U.S. Pat. No. 3,720,722)

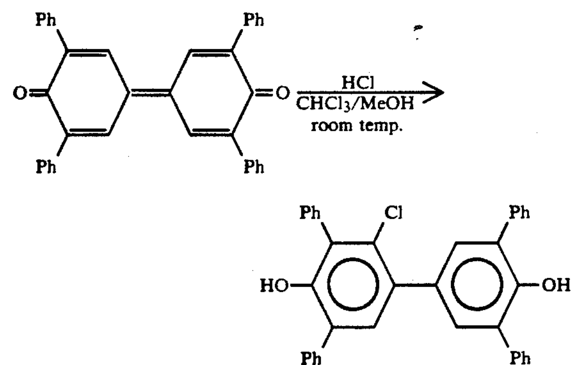

This reaction was carried out with 3,3',5,5'-tetraphenyldiphenoquinone (5 g) in a stirred mixture of chloroform (150 mL) and methanol (100 mL) by introducing gaseous hydrogen chloride into the reaction mixture at room temperature. The quinone was partly suspended in the mixture. The reaction mixture was kept under a nitrogen blanket. After 6 hours the reaction mixture changed from dark violet to a clear solution. The product was isolated by evaporation of the solvents and recrystallized by dissolving the product in hot chloroform and adding methanol to give 2-chloro-3,3',5,5'-tetraphenyl-[1,1'-biphenyl]-4,4'-diol (85% yield).

Example 15. Synthesis of a Polyester

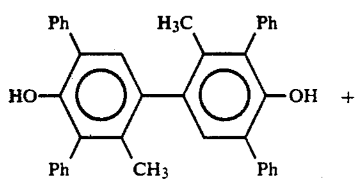

-continued

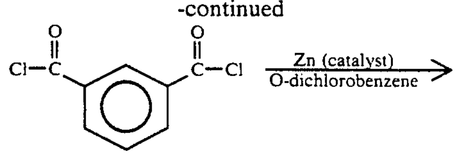

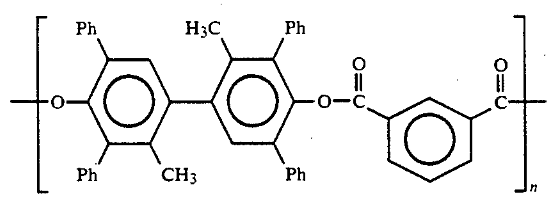

1 g (2 mmols) of 2,2'-dimethyl-3,3',5,5'-tetraphenyl-[1,1'-biphenyl]-4,4'-diol), 0.4 g (2 mmoles) of isophthaloyl dichloride and 8 mL of o-dichlorobenzene and a small amount of zinc as a catalyst were charged in 25 mL three neck flask. The mixture was heated upto the reflux temperature (175° C.) and kept at that temperature for 6 hours. The solution appeared very viscous and o-dichlorobenzene (3 mL) was added to dilute the solution. The solution was filtered and precipitated in methanol (98% yield). The resulting polymer was not soluble in chloroform, methylene chloride or acetone, but dissolved in hot o-dichlorobenzene and NMP. The polymer had an inherent viscosity of 0.26 in NMP. Tg is 233° C. and Tm is 402° C.

Polyetherimides

Preparation of Monomers

Example 16.

(4,4'-bis(3,4-dicarboxyphenoxy)2,2'-dimethyl 3,3',5,5'-tetraphenylbibenzenedianhydride)

To a 50 mL three necked round bottom flask equipped with a Dean-Stark trap and condenser was added, 8 g (15.4 mmol) of 2,2'-dimethyl-3,3',5,5'-tetraphenyl-[1,1'-biphenyl]-4,4'-diol, 7.9 g (38.3 mmol) of 4-nitro-N-methylphthalimide, and 20 mL of toluene. The reaction mixture was stirred and 6.8 g of potassium carbonate was added. The reaction mixture was heated to reflux (150° C.) for 3 hours until the water of reaction was removed. Tolene was removed from the tap untill the temperature rose to about 160° C. and the reaction was maintained under nitrogen atmosphere at this temperature for 10 hours. The reaction mixture was precipitated in a miture solution of methanol (150 mL) and water 50 mL) and isolated by filtration and dried. There was obtained 9.8 g of crude product (87% purity by HPLC, 85% yield). Recrystallization from ispropyl alcohol gave fine white crystals (98% purity by HPLC, 82% yield) melting at 234°-236° C. 1H NMR (200 MHz, CDCl3) δ200 (s, 6H, CH3) δ3.08 (s, 6H, N—CH3) δ6.75-7.65 (m, 28H).

A mixture of 9.0 g (10.8 mmol) of 4,4'-bis(N-methylphthalimide-4-oxy)2,2'dimethyl 3,3',5,5'tetraphenylbibenzene, 60 mL of isopropylalcohol, 20 mL of water and 20 g of 50% of sodium hydroxide was stirred at reflux for 5 hours, and then 20 mL of water was added. Acidification of the hot solution with hydrochloric acid was carried out over 2 hours and the reaction was then cooled down. The product was isolated by filtration and washed with hot water and dried. There was obtained 8.9 g (97% yield) of a white solid. The carboxyl group appeared as a broad peak at 3000–3300 $cm^{-1}$ in the IR. The product, 4,4'-bis(3,4 dicarboxyphenoxy) 2,2' dimethyl 3,3',5,5' tetraphenylbibenzene had m.p. 167°–169° C. 1H NMR (200 MHz, $CD_3OD$) δ6.60–7.67 (m, ArH).

A mixture of 9.0 (10.6 mmol) of 4,4'-bis(3,4-dicarboxyphenoxy) 2,2'-dimethyl 3,3',5,5'-teraphenylbibenzene, 60 mL of glacial acetic acid and 5 mL of acetic anhydride was stirred at reflux for 5 hours until a white solid separated. There was obtained 7.8 g (90% yield) of product which was purified by recrystallization from toluene/aceticacid; m.p.: 275°–278° C. 1H NMR (200 MHz, CDCl3) δ2.01(s, 6H, CH3) δ6.90–7.63 (m, 28H, ArH).

Example 17.

(4,4'-bis(3,4-dicarboxyphenoxy)2,2',3,3',5,5'-hexaphenylbibezenedianhydride)

A mixture of 8 g (12.4 mmol) of 2,2',3,3',5,5'-hexaphenyl-[1,1'-biphenyl]-4,4'-diol and 6.2 g (30.1 mmol) of 4-nitro N-methylphthalimide was placed in a 100 mL three-neck flask equipped with a Dean-Stark trap and a stirrer. The mixture was stirred and heated under nitrogen for 3 hours during which time the water was azeotropically removed and then maintained at 160° C. for 10 hours. After cooling, the solution was poured into a mixture of water (50 mL) and methanol (150 mL) and then the crude white precipitate was collected by filtration. The filtrate was thoroughly washed with water and hot methanol and dried under vacuum. It was crystallized from acetonitrile and chloroform. The yield of product was 10.5 g (88%). m.p. 268°–270° C. 1H NMR (200 MHz, CDCl3) δ3.06(s, 6H, CH3) δ6.60–7.45(m, 38H, ArH).

A mixture of 9.0 g (9.4 mmol) of 4,4'-bis(N-methyl phthalimide-4-oxy)2,2'dimethyl 3,3',5,5'hexaphenylbibenzene, 40 mL of isopropyl alcohol, 20 mL of methanol, 15 mL of water and 15 g of 50% sodium hydroxide was stirred at reflux for 3 hours. Water (50 mL) was added and the resulting mixture was acidified with hydrochloric acid. The white solid was filtered and washed with hot water and then dried under vacuum. The yield of product was 8.8 g (96%) m.p.: 169–172. 1H NMR (200 MHz, CD30D) δ6.78–8.03 (m, ArH).

A mixture of 12 g of 4,4'-bis(3,4-dicarboxyphenoxy)2,2',3,3',5,5'-hexaphenylbibenzene, 50 mL of glacial acetic acid and 5 Ml of acetic anhydride was stirred at reflux for 4 hours during which time a white solid was precipitated and removed by filtration. It was washed twice with acetic acid and water and then dried under vacuum (7.1 g, 93% yield). m.p. 305°–307° C. 1H NMR (200 MHz, CDCl3) δ6.77–7.55 (m, ArH).

Example 18.

(4,4'-bis(3,4-dicarboxyphenoxy)3,3',5,5'-tetraphenylbibenzenedianhydride)

A mixture of 7.5 g (15.2 mmol) of 3,3',5,5'-tetraphenyl-[1,1'-biphenyl]-4,4'-diol, 9.4 g 45.6 mmol) of 4-nitro-N-methyl phthalimide, 6.7 g of potassium carbonate, 50 mL of DMAc and 25 mL of toluene was stirred under a nitrogen atmosphere at reflux in a three necked flask equipped with a Dean-Stark trap for 3 hours. During this time water and toluene were azeotropically removed. The reaction was kept at 165° C. for 10 hours. The solution was precipitated in a mixture of water (50 mL) and methanol (150 mL). A crude product (10.6 g, 86% yield) was isolated by filtration and washed with hot methanol and recrystallized from ethyl acetate and then dried in vacuum (98% purity by HPLC); m.p. 254°–255° C. 1H NMR (200 MHz, CDCl3) δ3.05 (s, 6H, CH3) δ6.85–7.77 (m, ArH).

A mixture of 7.5 g (9.3 mmol) of 4,4'-bis(N-methylphthalimid-4-oxy)3,3',5,5'-tetraphenylbibenzene, 100 mL of methanol, 50 mL of water and 20 g of 50% sodium hydroxide was stirred at reflux for 7 hours. A product separated after the aqueous solution was acidified. The crude material was isolated by filtration and the product was then mixed with 15 g of 50% sodium hydroxide, 50 mL of water and 150 mL of methanol. It was heated at reflux for 3 hours. Acidification of the solution with concentrated hydrochloric acid gave 7.5 g (98% yield) of product. m.p. 173°–176° C.

A mixture of 7.0 g (8.5 mmol) of 4,4'-bis(3,4-dicarboxyphenoxy)3,3',4,4'-tetraphenylbibenzene, 60 mL of acetic acid and 6 mL of acetic anhydride was stirred at reflux for 5 hours. The solution was cooled and filtered. The yield was 5.7 g (85%). m.p. 276°–279° C. 1H NMR (200 MHz, CDCl3) δ7.05–7.79 (m, ArH).

Polymerization

The synthesis of polyetherimides is given below as a general procedure. To a 50 mL round bottom flask was added 1 g (1.23 mmol) of 4,4'-bis(3,4-dicarboxyphenoxy) 2,2-dimethyl 3,3',5,5' tetraphenylbibezenedianhydride, 0.133 g (1.23 mmol) of m-phenylenediamine and 8 mL of distilled N-methyl-2-pyrrolidinone. The flask was purged with nitrogen and the solution was stirred for 3 hours under a nitrogen atmosphere at room temperature. The solution became viscous as the polyamic acid formed. Then 4 mL of chlorobezene was added. The reaction system was heated to reflux with stirring for 3 hours while the the chlorobezene was distilled off and the water removed by azeotropic distillation. The reaction mixture was cooled and precipitated into a large excess of methanol. The polyimides were separated by filtration and dried in a vacuum oven.

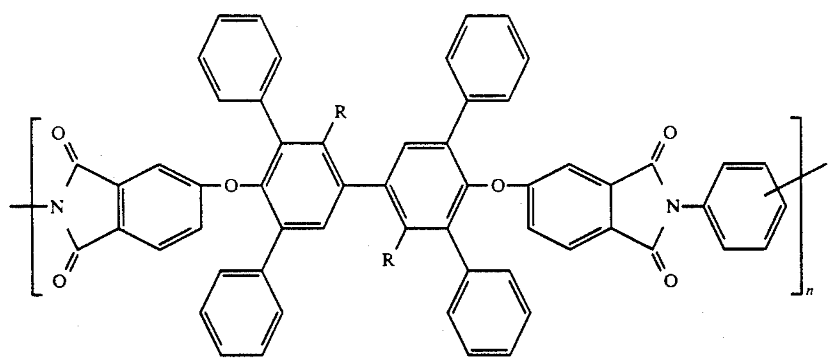

| Example | R | Diamine | Tg | TGA (−5%) (air) | ηinh | Mw × $10^3$ | Mw/Mn |
|---|---|---|---|---|---|---|---|
| 19 | $CH_3$ | p | | 513 | 0.27 | 39.4 | 1.63 |
| 20 | | m | 290 | 417 | 0.26 | 37.1 | 1.57 |
| 21 | Ph | p | 300 | 553 | 0.16 | 25.5 | 2.00 |
| 22 | | m | 260 | 554 | 0.14 | 25.0 | 1.85 |
| 23 | H | p | 273 | 522 | 0.22 | 10.7 | 2.74 |
| 24 | | m | 268 | 520 | 0.13 | 15.6 | 2.13 |

Copolymerization

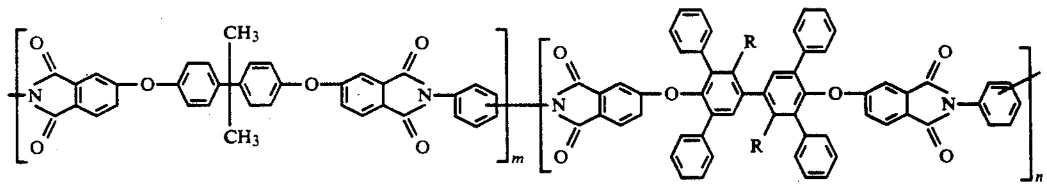

The same reaction as above was performed for 3 hours using 0.5 g (0.616 mmol) of 4,4' bis (3,4-dicarboxyphenoxy)2,2'-dimethyl 3,3',5,5' tetraphenylbibezenedianhydride and 0.31 g (0.616 mmol) of BPA diphthalic anhydride and 0.129 g (1.23 mmol) of p-phenylenediamine and 7 mL of NMP. The reaction mixture was treated in the same manner as above.

| Example | R | Diamine | Tg | TGA (−5%) air | ηinh | Mw/ $10^3$ | Mw/ Mn |
|---|---|---|---|---|---|---|---|
| 25 | $CH_3$ | p | 283 | 508 | 0.31 | 36.2 | 2.57 |
| 26 | | m | 240 | 501 | 0.18 | 14.2 | 2.33 |
| 27 | Ph | p | 277 | 404 | 0.22 | 24.0 | 2.88 |
| 28 | | m | 255 | 453 | 0.18 | 26.5 | 2.63 |
| 29 | H | p | 215 | 492 | 0.21 | 11.5 | 1.98 |
| 30 | | m | 247 | 527 | 0.19 | 30.3 | 1.90 |

We claim:

1. A homopolymer or copolymer containing units of formula:

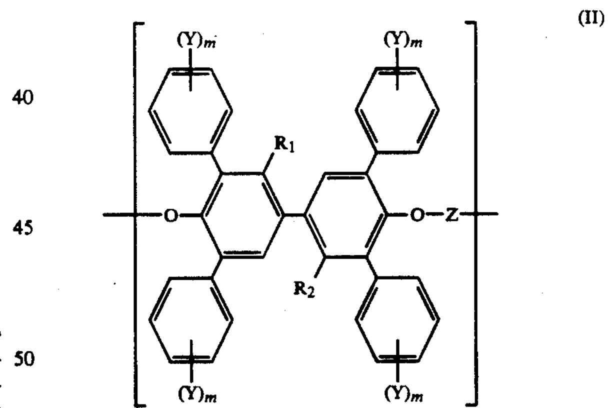

(II)

wherein $R_1$ and $R_2$ are the same and are selected from methyl, phenyl, naphthyl, p-fluorophenyl, p-chlorophenyl and p-bromophenyl, or one of $R_1$ and $R_2$ is hydrogen and the other is chlorine;

y is fluorine;

m is 0, 1, 2, 3, 4 or 5; and

Z is a divalent linkage of formula:

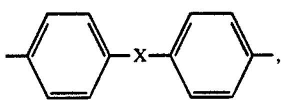

in which X is —CO— or —$SO_2$—; or

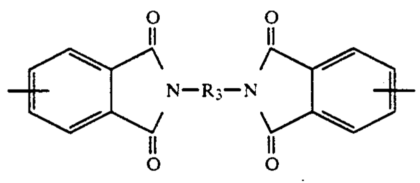

in which $R_3$ is an aromatic hydrocarbon radical or aromatic hydrocarbon ether radical having from 6 to 20 carbon atoms, and halogenated derivatives thereof.

2. A homopolymer or copolymer of claim 1, in which $R_1$ and $R_2$ are methyl or phenyl and m is 0.

3. A homopolymer or copolymer containing units of formula:

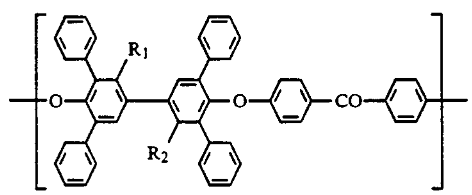

wherein $R_1$ and $R_2$ are methyl or phenyl.

4. A homopolymer or copolymer containing units of formula:

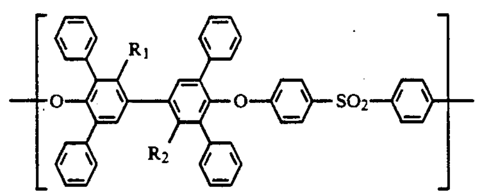

wherein $R_1$ and $R_2$ are methyl or phenyl.

5. A process for producing a homopolymer or copolymer of formula (V):

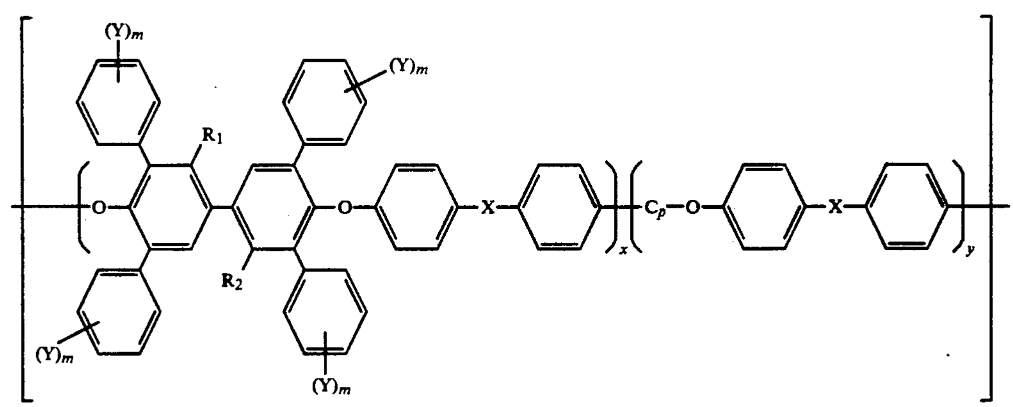

wherein $R_1$ and $R_2$ are the same and are selected from methyl, phenyl, naphthyl, p-fluorophenyl, p-chlorophenyl and p-bromophenyl, or one of $R_1$ and $R_2$ is hydrogen and the other is chlorine;

X is a radical —CO— or —$SO_2$—;

Y is fluorine;

m is 0, 1, 2, 3, 4 or 5;

x is an integer of at least 1;

y is 0 or an integer of 1 or more;

$x+y=n$, and n is an integer of 2 to 200; and $C_p$ is derived from a comonomer, comprising reacting a biphenol of formula (III):

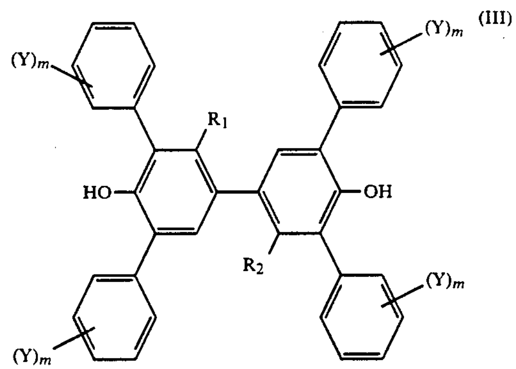

in which $R_1$, $R_2$, Y and m are as defined above, and a comonomer, if desired, with a compound of formula (VI):

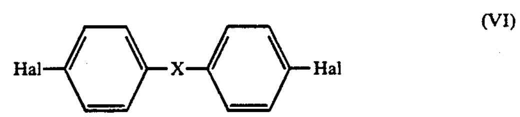

in which Hal is fluorine or chlorine and X is as defined above.

6. A process according to claim 5, in which said reacting is carried out in the presence of a base in a polar aprotic solvent.

7. A process according to claim 6, in which said base is potassium carbonate.

8. A process according to claim 6, in which $R_1$ and $R_2$ are methyl or phenyl, m is 0, X is —CO— and y is 0.

9. A process according to claim 6, in which $R_1$ and $R_2$ are methyl or phenyl, m is 0, X is —$SO_2$— and y is 0.

10. A process according to claim 7, carried out under reflux.

* * * * *